US007787685B2

(12) United States Patent
Huang et al.

(10) Patent No.: US 7,787,685 B2
(45) Date of Patent: Aug. 31, 2010

(54) EXTRACTING ORDINARY AND EXTRAORDINARY OPTICAL CHARACTERISTICS FOR CRITICAL DIMENSION MEASUREMENT OF ANISOTROPIC MATERIALS

(75) Inventors: Jacky Huang, Hsin-Chu (TW);
Chin-Ming Ke, Hsin-Chu (TW);
Tsai-Sheng Gau, Hsin-Chu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 1042 days.

(21) Appl. No.: 11/467,023

(22) Filed: Aug. 24, 2006

(65) Prior Publication Data

US 2007/0242263 A1   Oct. 18, 2007

Related U.S. Application Data

(60) Provisional application No. 60/792,560, filed on Apr. 17, 2006.

(51) Int. Cl.
*G06K 9/00* (2006.01)

(52) U.S. Cl. .................................... 382/141; 382/144

(58) Field of Classification Search .......... 257/E21.206; 324/642; 356/504, 517, 937, FOR. 123; 378/34, 35; 382/141, 144; 428/824.5, 848.8; 438/7, 9; 700/121; 850/9
See application file for complete search history.

(56) References Cited

U.S. PATENT DOCUMENTS

| 6,441,902 B1 | 8/2002 | Hilfiker et al. |
| 2004/0038537 A1* | 2/2004 | Liu et al. ............ 438/694 |
| 2005/0048222 A1* | 3/2005 | Ruelke et al. ........ 427/579 |
| 2005/0153564 A1* | 7/2005 | Mak et al. ............ 438/710 |
| 2005/0179004 A1* | 8/2005 | Morishima et al. .... 252/299.01 |

(Continued)

FOREIGN PATENT DOCUMENTS

WO   WO 02/15238 A2   2/2002

(Continued)

OTHER PUBLICATIONS

Dang Met Al, "Ellipsometric Spectra and Optical Properties of Anisotropic SrBi2Ta2O9 Films", Chinese Physics Letters, Chinese Physical Society and IOP Publishing Ltd., pp. 266-268, vol. 21, No. 2, Feb. 2004.*

(Continued)

*Primary Examiner*—Bhavesh M Mehta
*Assistant Examiner*—Gregory F Cunningham
(74) *Attorney, Agent, or Firm*—Haynes and Boone, LLP

(57) ABSTRACT

Methods and apparatus for measuring a critical dimension of an optically-anisotropic feature, including extracting a number of values each descriptive of the optically-anisotropic feature, including values corresponding to ordinary and extraordinary measurements of one or more optical characteristics of the optically-anisotropic feature. The optical characteristics can include the index of refraction and/or the extinction coefficient of the optically-anisotropic feature, among others. Additionally, the values can be input into an optical critical dimension (OCD) measurement model, such that the critical dimension can be verified via optical measurement based on the OCD measurement model. The optical measurement of the critical dimension can also be verified via scanning electron microscope (SEM) measurement. Furthermore, the optically-anisotropic feature may have a substantially amorphous composition, such as amorphous carbon, including where the optically-anisotropic feature is that of a hardmask substantially comprising amorphous carbon or otherwise having a substantially amorphous composition.

18 Claims, 10 Drawing Sheets

U.S. PATENT DOCUMENTS

2007/0153272 A1    7/2007    Liou et al.

OTHER PUBLICATIONS

S. Takeuchi et al, "New Ellipsometric Approach to Critical Dimension Metrology Utilizing Form Birefringence Inherent in a Submicron Line-and-Space Pattern", Japanese Journal of Applied Physics, Japan Society of Applied Physics, Tokyo, Japan, pp. 7720-7725, vol. 36, No. 12B, Dec. 1, 1997.

En Naciri A et al, "Spectroscopic Generalized Ellipsometry Based On Fourier Analysis", Applied Optics, Optical Society of America, pp. 4802-4811, vol. 38, No. 22, Aug. 1, 1999.

Dang M et al, "Ellipsometric Spectra and Optical Properties of Anisotropic SrBi2Ta2O9 Films", Chinese Physics Letters, Chinese Physical Society and IOP Publishing Ltd., pp. 266-268, vol. 21, No. 2, Feb. 2004.

Leng J et al, "Multi-Technology Measurements of Amorphous Carbon Films", Micro and Nanosystems Materials And Devices Symposium (Materials Research Society Symposium Proceedings vol. 872), Materials Research Society Warrendale, PA, pp. J17.5.1-J17.5.6, vol. 872, 2005.

Search Report issued by Netherlands Patent Office, Application No. NL2000563, Feb. 20, 2009.

\* cited by examiner

EXTRACTING ORDINARY AND EXTRAORDINARY OPTICAL CHARACTERISTICS FOR CRITICAL DIMENSION MEASUREMENT OF ANISOTROPIC MATERIALS

CROSS REFERENCE

This application claims priority to U.S. Patent Application Ser. No. 60/792,560 filed on Apr. 17, 2006 which is hereby incorporated by reference.

BACKGROUND

Hardmasks and other photomasks are often utilized in lithography systems to manufacture the ICs, where successful production can require features on such photomasks have desired and uniform sizes. Accordingly, photomask manufacturers routinely evaluate feature sizing performance by measuring specific features in order to ensure that the photomasks include features that have the desired and uniform sizes. The features that are evaluated are generally referred to as critical dimensions (CDs), and are measured via optical systems and/or scanning electron microscopes (SEMs).

Optical metrology tools include reflectometers, ellipsometers, spectroscopic reflectometers, spectroscopic ellipsometers, polarized beam reflectometers, polarized beam spectroscopic reflectometers, scatterometers, spectroscopic scatterometers and optical CD measurement tools. Optical CD (OCD) measurement is useful because often only one measurement is required to analyze CDs, profiles, thicknesses, and sidewall angles without fracturing the wafer. However, as feature sizes have decreased below resolution limits of many OCD measurement tools, the use of SEMs has increased. Nonetheless, multiple optical and/or electron microscope instruments can be combined on a common platform to comprise a single metrology instrument that incorporates multiple spectroscopic metrology capabilities. In such arrangements, one or more processors may be utilized to analyze output signals generated by various detectors, processing the output signals individually or in combination to evaluate the characteristics of a sample.

Hardmasks formed by ash removable deposition (ARD) processing, particularly hardmasks comprising amorphous carbon, has recently gained popularity as a new approach for IC patterning. Amorphous carbon has a low etching rate, thus making its utilization beneficial when subsequent processing includes oxide or silicon dry etching. Additionally, amorphous carbon is easily removed by $O_2$ plasma. Hence, patterning and stripping such hardmasks have little impact on profiles and CDs of features defined in underlying layers. Amorphous carbon also provides a high extinction coefficient k, which is beneficial during lithographic patterning. However, current optical measurement methods, such as ellipsometry and reflectometry, only extract the ordinary refractive index n and extinction coefficient k which are insufficient to accurately characterize amorphous carbon and other optically anisotropic materials.

BRIEF DESCRIPTION OF THE DRAWINGS

The present disclosure is best understood from the following detailed description when read with the accompanying figures. It is emphasized that, in accordance with the standard practice in the industry, various features may not be drawn to scale. In fact, the dimensions of the various features may be arbitrarily increased or reduced for clarity of discussion.

DETAILED DESCRIPTION

Figure 1:
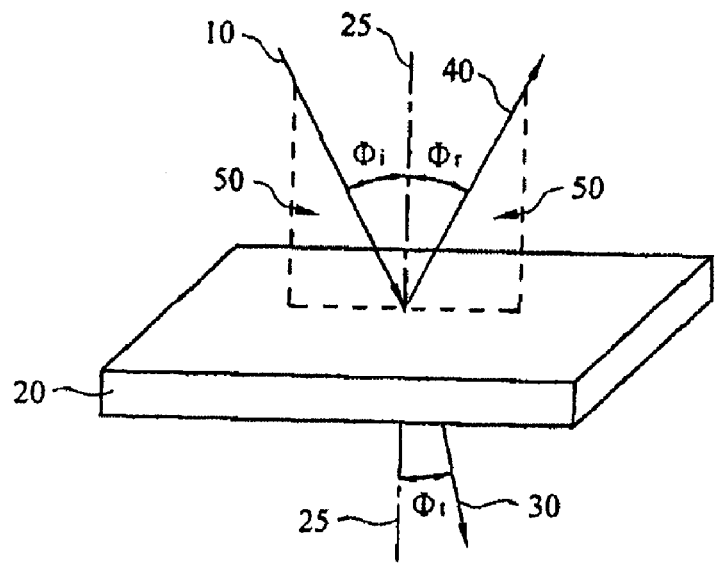
FIG. 1 is a schematic view of a light beam incident on a sample, demonstrating aspects related to the prior art and the present disclosure.

It is to be understood that the following disclosure provides many different embodiments, or examples, for implementing different features of various embodiments. Specific examples of components and arrangements are described below to simplify the present disclosure. However, these are merely examples, and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Ellipsometry and/or reflectometry are often employed to characterize the optical constants and thickness of thin films, including hardmasks and other photomasks. Such techniques are sensitive to several material characteristics, such as layer thickness, optical constants (refractive index and extinction coefficient), surface roughness, composition, and optical anisotropy. For example, these characteristics are determinable from transmission and reflection intensity data obtained via utilization of a reflectometer, and/or transmission, reflection intensity and ellipsometry obtained via utilization of an ellipsometer.

Referring to FIG. 1, illustrated is a schematic of a beam of light 10 incident on a sample 20 at an angle of incidence $\Phi_i$, demonstrating the resulting transmitted beam 30 and reflected beam 40. The angle of incidence $\Phi_i$ is defined as the angle between the direction of the input beam 10 and the direction normal to the sample 20 (designated in FIG. 1 by reference numeral 25). At the boundary between mediums (the boundary between the sample 20 and the air or other ambient environment), part of the input beam 10 will be reflected from the sample 20 as the reflected beam 40 at angle $\Phi_r$, while another part of the input beam 10 will be transmitted through the sample 20 as the transmitted beam 30 at angle $\Phi_t$. Snell's law requires that all three of the input beam 10, the transmitted beam 30, and the reflected beam 40 be in the plane of incidence 50. The plane of incidence 50 is defined as that plane which contains the input beam 10, the output beams 30 and 40, and the normal direction 25 of the sample 20.

The measurements described above may acquire the transmission intensity ratio T and reflection intensity ratio R over a given range of wavelengths. T is defined as the ratio of the transmitted light intensity $I_t$ and the incident light intensity $I_i$, as shown in Equation (1):

$$T = I_t/I_i \qquad (1)$$

R is defined as the ratio of the reflected light intensity $I_r$ and the incident light intensity $I_i$, as shown in Equation (2):

$$R = I_r/I_i \qquad (2)$$

Ellipsometry measures the change in polarization state of light reflected from the surface of a sample. The measured values are expressed as $\Psi$ and $\Delta$. These values are related to the ratio of Fresnel reflection coefficients, $R_p$ and $R_s$, for p- and s-polarized light, respectively, by Equation (3):

$$\tan(\Psi)e^{i\Delta} = R_p/R_s \qquad (3)$$

Because ellipsometry measures the ratio of two values, it can be highly accurate and very reproducible. From Equation (3), the ratio is seen to be a complex number containing "phase" information in $\Delta$, which makes the measurement very sensitive.

Figure 2:
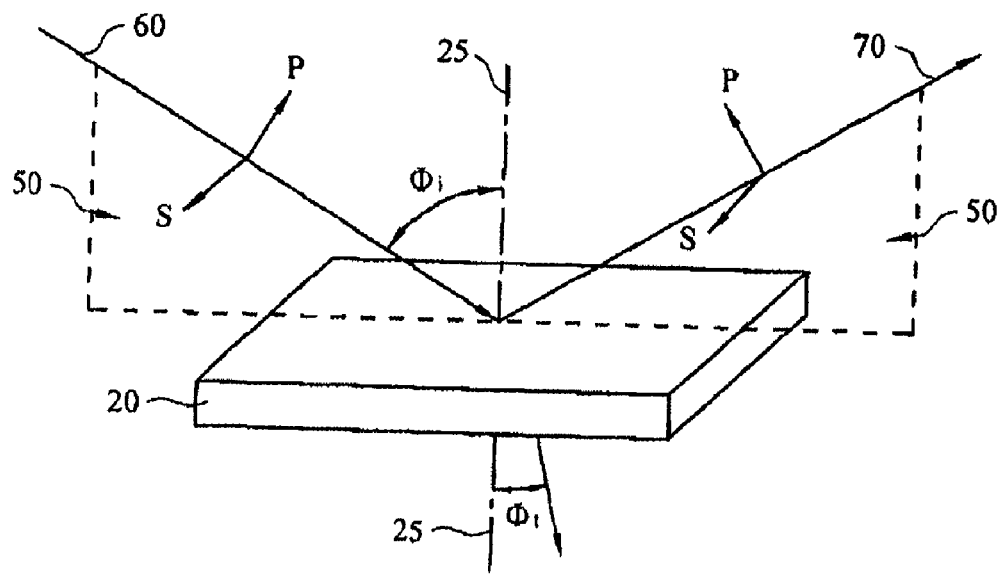
FIG. 2 is another schematic view of a light beam incident on a sample, demonstrating aspects related to the prior art and the present disclosure.

Referring to FIG. 2, illustrated is a schematic of a linearly polarized input beam 60 that is converted to an elliptically polarized reflected beam 70. For an angle of incidence $\Phi_i$ greater than 0° and less than 90°, p-polarized light and s-polarized will be reflected differently.

The coordinate system used to describe the ellipse of polarization is the p-s coordinate system. The p-direction is taken to be perpendicular to the direction of propagation and contained in the plane of incidence 50. The s-direction is taken to be perpendicular to the direction of propagation and parallel to the surface of the sample 20.

Optical constants define how light interacts with a material. The complex refractive index is a representation of the optical constants of a material, as shown in Equation (4):

$$\tilde{n} = n + ik \qquad (4)$$

The real part, or index of refraction n, defines the phase velocity of light in material, which is defined by Equation (5):

$$v = c/n \qquad (5)$$

where v is the speed of light in the material and c is the speed of light in vacuum. The imaginary part, or extinction coefficient k, determines how fast the amplitude of the wave decreases. The extinction coefficient k is directly related to the absorption of a material and is related to the absorption coefficient $\alpha$ by Equation (6):

$$\alpha = 4\pi k/\lambda \qquad (6)$$

where $\alpha$ is the absorption coefficient and $\lambda$ is the wavelength of light.

Figure 3:
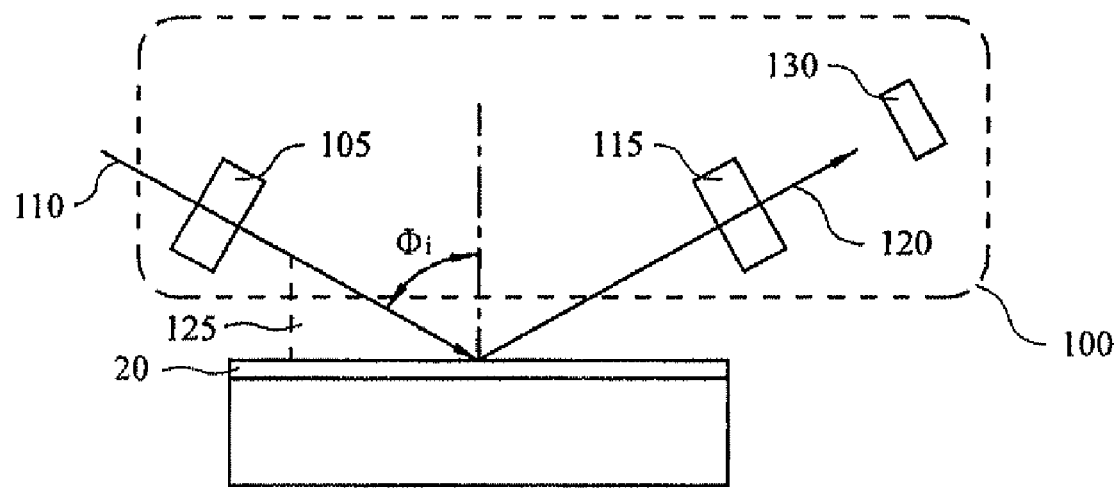
FIG. 3 is a schematic view of at least a portion of one embodiment of apparatus according to aspects of the present disclosure.

There are many ways to measure the reflection and transmission properties described above. One example is by polarization-sensitive reflectivity. FIG. 3 is a schematic view of at least a portion of one embodiment of apparatus 100 that may be employed in polarization-sensitive reflectivity in accord with one or more aspects of the present disclosure. The apparatus 100 includes a polarizer 105 through which an input beam 110 passes prior to incidence on the sample 20. The apparatus 100 also includes a polarizer 115, often referred to in this context as the "analyzer," through which passes the resulting reflected beam 120. A detector 130 is positioned to detect one or more characteristics of the reflected beam 120, such as intensity and/or phase, whether constant or time-dependent. The detector 130 may be integral to the apparatus 100, as depicted in FIG. 3, or otherwise associated with the apparatus 100.

After polarization via the polarizer 105, the input beam 110 interacts with the sample 20 at an angle of incidence $\Phi_i$. The reflected beam 120 is then re-polarized via the analyzer 115 before its intensity is detected. At a large angle of incidence $\Phi_i$, there is a significant difference in the reflectance for s- and p-polarized light, so there are two pieces of information that can be obtained about the sample 20 at each wavelength of the input beam 110, as represented by Equations (7) and (8):

$$R_p = r_p r_p^* \qquad (7)$$

$$R_s = r_s r_s^* \qquad (8)$$

These quantities are measured by aligning the polarizer 105 and the analyzer 115 in either the s or the p orientation. The apparatus 100 can also be used as an example for the calculation using Mueller matrices. For the p measurement, the polarizer 105 and the analyzer 115 are aligned parallel to the plane of incidence 125, such that:

$$\theta_0 = \theta_1 = 0° \qquad (9)$$

where $\theta_0$ is the polarization angle of the polarizer 105 (e.g., orientation of the fast axis relative to a principal frame of reference) and $\theta_1$ is the polarization angle of the analyzer 115 (e.g., orientation of the fast axis relative to the same principal frame of reference). Subsequent Mueller matrix multiplication yields:

$$I_p = I_0 R_p \qquad (10)$$

For the s measurement, the polarizer 105 and the analyzer 115 are aligned perpendicular to the plane of incidence 125, such that:

$$\theta_0 = \theta_1 = 90° \qquad (11)$$

and $$I_s = I_0 R_s \qquad (12)$$

Figure 4:
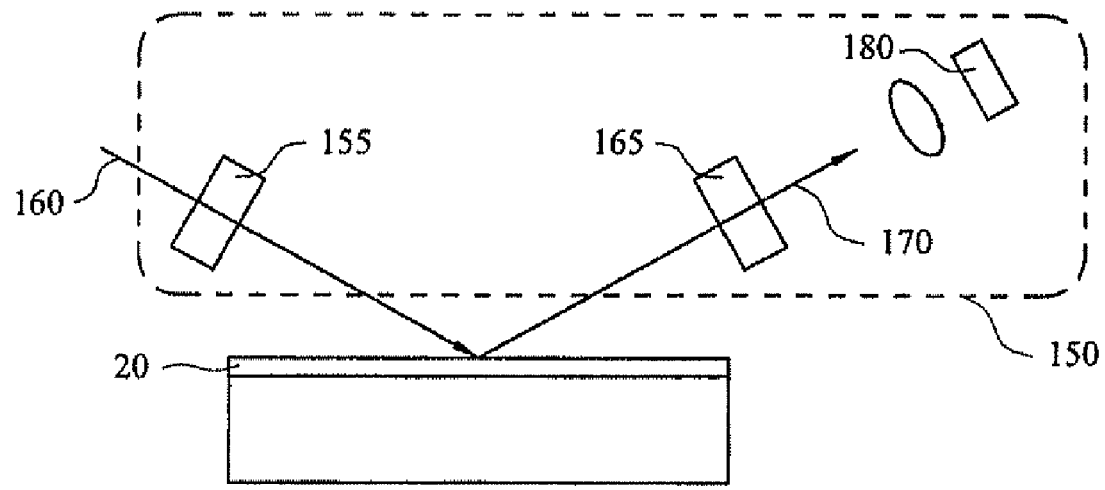
FIG. 4 is a schematic view of at least a portion of another embodiment of apparatus according to aspects of the present disclosure.

Another technique for measuring the above-described reflection and transmission properties in accord with one or more aspects of the present disclosure is rotating analyzer ellipsometry (or rotating polarizer ellipsometry). FIG. 4 is a schematic view of at least a portion of one embodiment of apparatus 150 that may be employed in rotating analyzer ellipsometry in accord with one or more aspects of the present disclosure. The apparatus 150 includes a polarizer 155 through which an input beam 160 passes prior to incidence on the sample 20. The apparatus 150 also includes an analyzer 165 through which passes the resulting reflected beam 170. A detector 180 is positioned to detect one or more characteristics of the reflected beam 170, such as intensity and/or phase, whether constant or time-dependent. The detector 180 may be integral to the apparatus 150, as depicted in FIG. 4, or otherwise associated with the apparatus 150.

The analyzer 165 is configured to be physically rotated so that the azimuthal angle of the analyzer 165 is given by:

$$\theta_1 = \omega t \quad (13)$$

Alternatively, where the polarizer 155 is configured to be physically rotated instead of the analyzer 165, such that the azimuthal angle of the polarizer 155 is given by:

$$\theta_0 = \omega t \quad (14)$$

The intensity of the reflected beam 170 after passing through the analyzer 165, as detected by the detector 180, is given by:

$$I(t) = I_{dc}[1 + a_1 \cos(2\omega t) + a_2 \sin(2\omega t)] \quad (15)$$

where $$I_{dc} = 1 - N \cos(2\theta_p) \quad (16)$$

$$a_1 = [\cos(2\theta_p) - N]/[1 - N \cos(2\theta_p)] \quad (17)$$

$$a_2 = [C \sin(2\theta_p)]/[1 - N \cos(2\theta_p)] \quad (18)$$

The associated ellipsometry parameters N and C in Equations (16)-(18), as well as ellipsometry parameter S, are represented by:

$$N = \cos(2\psi) \quad (19)$$

$$C = \sin(2\psi)\cos(\Delta) \quad (20)$$

$$S = \sin(2\psi)\sin(\Delta) \quad (21)$$

The angles $\psi$ and $\Delta$ are the traditional ellipsometry parameters, which are defined as:

$$\rho = r_p/r_s = \tan(\psi)\exp(i\Delta) = [C + iS]/[1 + N] \quad (22)$$

In one embodiment, the signal is normalized to the $I_{dc}$ term, and may not be directly measured. The two Fourier components $a_1$ and $a_2$ are functions of the fixed polarizer angle and the sample parameters N and C.

Figure 5:
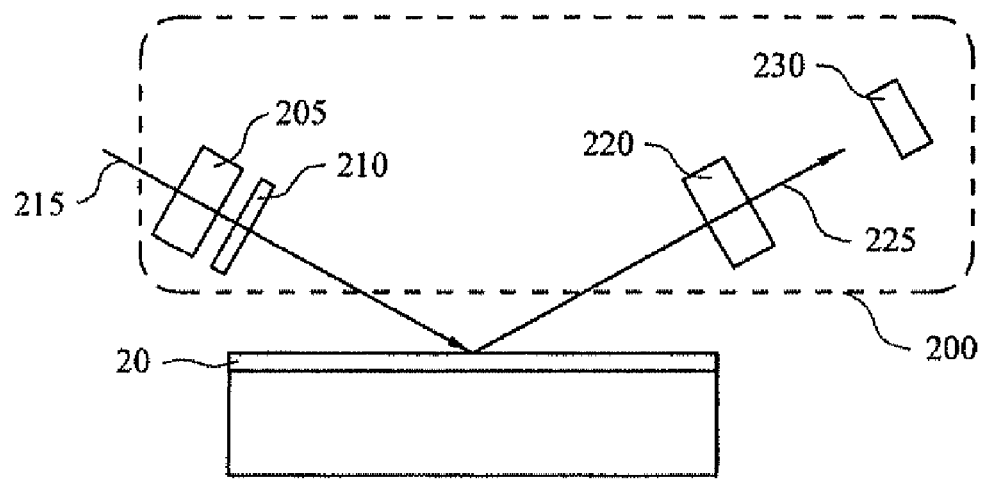
FIG. 5 is a schematic view of at least a portion of another embodiment of apparatus according to aspects of the present disclosure.

Another technique for measuring the above-described reflection and transmission properties in accord with one or more aspects of the present disclosure is nulling ellipsometry. FIG. 5 is a schematic view of at least a portion of one embodiment of apparatus 200 that may be employed in nulling ellipsometry in accord with one or more aspects of the present disclosure. The apparatus 200 includes a polarizer 205 and a compensator 210 through which an input beam 215 passes prior to incidence on the sample 20. The apparatus 200 also includes an analyzer 220 through which passes the resulting reflected beam 225. A detector 230 is positioned to detect one or more characteristics of the reflected beam 225, such as intensity and/or phase, whether constant or time-dependent. The detector 230 may be integral to the apparatus 200, as depicted in FIG. 5, or otherwise associated with the apparatus 200.

Measurements may be made with the apparatus 200 by rotating the azimuthal angle of the polarizer 205 ($\theta_0$) and the azimuthal angle of the analyzer 220 ($\theta_1$) to minimize the intensity of light incident upon the detector 230. Nulling ellipsometer measurements are made by fixing the azimuthal angle of the compensator 210, such as at $\theta_c = 45°$, and the degree of retardation of the compensator, such as at $\delta = \pi/2$, although other values are also within the scope of the present disclosure. Under these assumptions, the intensity at the detector 230 is given by:

$$I = 0.25 I_0 R\{1 - N \cos(2\theta_1) + \sin(2\theta_1)[C \sin(2\theta_0) + S \cos(2\theta_0)]\} \quad (23)$$

In one embodiment, the compensator 210 is designed for a specific wavelength (such as 633 nm) and its retardation is about (or precisely) $\pi/2$. However, other values are also within the scope of the present disclosure.

Another technique for measuring the above-described reflection and transmission properties in accord with one or more aspects of the present disclosure is rotating-analyzer ellipsometry with a compensator. Standard rotating-analyzer ellipsometers may be insensitive to the S parameter, and therefore not be able to measure $\Delta$ accurately when $\Delta$ is near 0° or 180°. One solution to this is to include a compensating element in the light path. FIG. 5 may also depict a rotating-analyzer ellipsometer 200 with a compensating element 210 after the polarizer 205, if modified in the respect that the analyzer 220 is rotated. The compensator 210 may be a quasi-achromatic compensator, where $\delta \sim \pi/2$. Assuming that the polarizer 205 is set at 45° with respect to the fast axis of the compensator 210, the intensity at the detector 230 is then given by:

$$I_{dc} = 1 - N \sin(2\theta_c)\cos(\delta) \quad (24)$$

where $$a_1 = [-\sin(2\theta_c)\cos(\delta) - N]/[1 - N \sin(2\theta_c)\cos(\delta)] \quad (25)$$

$$a_2 = [C \cos(2\theta_c)\cos(\delta) - S \sin(\delta)]/[1 - N \sin(2\theta_c)\cos(\delta)] \quad (26)$$

If the phase retardation of the compensator 210 is given by $\delta = \pi/2$, then $a_1 = -N$ and $a_2 = -S$. However, if the phase retardation of the compensator 210 is $\delta = 0$, the results are the same as for the rotating analyzer ellipsometer, described above.

Some ellipsometers use the scheme of nulling ellipsometers where the two polarizers (e.g., polarizer 205 and analyzer 220) are fixed and the compensator (e.g., compensator 210) is rotated. In such an arrangement, the light intensity incident upon the detector 230 becomes a function of time, much like the rotating analyzer ellipsometer described above. Because the compensator 210 is rotating between the sample 20 and the polarizer 205, there are two frequency components: $2\omega t$ and $4\omega t$. The intensity of the light beam incident upon the detector 230 is then given by:

$$I = I_{dc} + a_{2S}\sin(2\omega t) + a_{2C}\cos(2\omega t) + a_{4S}\sin(4\omega t) + a_{4C}\cos(4\omega t) \quad (27)$$

The values of the five coefficients shown in Equation (27) depend upon the retardation of the compensator $\delta$, which will also be a function of wavelength, as well as the azimuthal angles $\theta_p$ and $\theta_a$. For this to be a complete ellipsometer (that is, where N, S and C are all measured), $\theta_a$ must not be close to 0° or 180°. If it is assumed that $\theta_a = 45°$, then the five coefficients are given by:

$$I_{dc} = 1 + 0.5[1 + \cos(\delta)][C \sin(2\theta_p) - N \cos(2\theta_p)] \quad (28)$$

$$a_{2S} = S \sin(\delta)\cos(2\theta_p) \quad (29)$$

$$a_{2C} = S \sin(\delta)\sin(2\theta_p) \quad (30)$$

$$a_{4S} = 0.5[1 - \cos(\delta)][C \cos(2\theta_p) - N \sin(2\theta_p)] \quad (31)$$

$$a_{4C} = -0.5[1 - \cos(\delta)][C \sin(2\theta_p) + N \cos(2\theta_p)] \quad (32)$$

Accordingly, this ellipsometer is capable of measuring N, S and C for all values of $\theta_p$.

Figure 6:
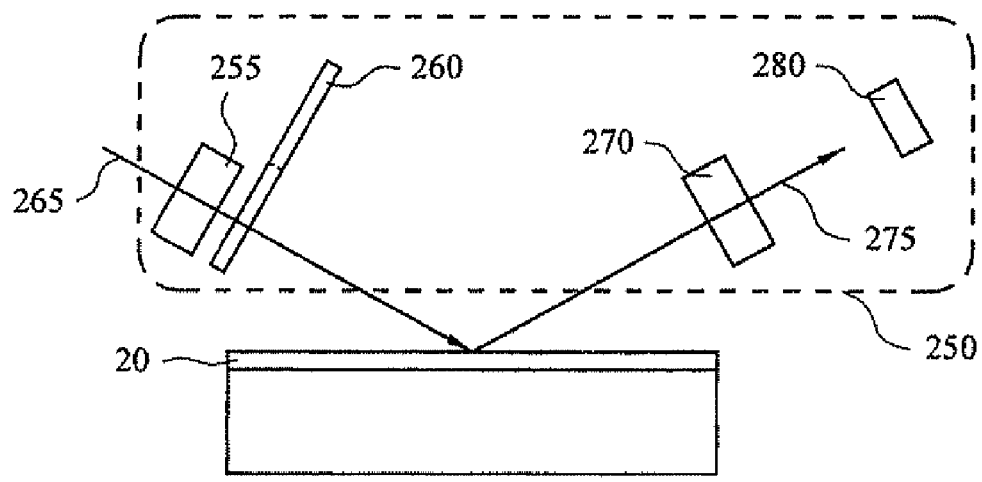
FIG. 6 is a schematic view of at least a portion of another embodiment of apparatus according to aspects of the present disclosure.

Another technique for measuring the above-described reflection and transmission properties in accord with one or more aspects of the present disclosure is polarization modulation ellipsometry. Polarization modulation ellipsometers are generally defined as ellipsometers that use a modulation technique other than the physical rotation of one or more optical elements. FIG. 6 is a schematic view of at least a portion of one embodiment of apparatus 250 that may be employed in polarization modulation ellipsometry in accord with one or more aspects of the present disclosure. The apparatus 250 includes a polarizer 255 and a photoelastic modulator (PEM) 260 through which an input beam 265 passes prior to incidence on the sample 20. The apparatus 250 also includes an analyzer 270 through which passes the resulting reflected beam 275. A detector 280 is positioned to detect one or more characteristics of the reflected beam 275, such as intensity and/or phase, whether constant or time-dependent. The detector 280 may be integral to the apparatus 250, as depicted in FIG. 6, or otherwise associated with the apparatus 250.

The PEM 260 is generally used to generate a time-dependent polarization state, although it is also possible to use electro-optic modulators. Although there are several designs within the scope of the present disclosure, all share a common description. The PEM 260 is a time-dependent compensator, where the retardation $\delta(t)=A\sin(\omega t)$, the modulation amplitude A being proportional to the driving force of the modulator. In its operation, an optical element is set into physical oscillation by some external driving force. If the optical element of the PEM 260 is momentarily in compression, then the refractive index along the compressive direction is higher than the refractive index would be in the unstrained optical element, while the refractive index perpendicular to the compressive direction is lower. Similarly, if the optical element of the PEM 260 is momentarily in expansion, then the refractive index along the expansive direction is lower, but the refractive index perpendicular to the expansive direction is higher than in the unstrained optical element. The Mueller matrix for the PEM 260 is the Mueller matrix for a compensator where $\delta(t)=A\sin(\omega t)$.

The basis functions for rotating element ellipsometers are of the form $\sin(n\omega t)$ and $\cos(n\omega t)$, where n is an integer, such that standard Fourier analysis can be used. The basis functions for polarization modulation ellipsometers are of the form $X=\sin[A\sin(\omega t)]$ and $Y=\cos[A\sin(\omega t)]$. These basis functions can be expressed in terms of an infinite series of sines and cosines, using integer Bessel functions as coefficients:

$$X = \sin[A\sin(\omega t)] = 2\sum_{j=1} J_{2j-1}(A)\sin[(2j-1)\omega t] \quad (33)$$

$$Y = \cos[A\sin(\omega t)] = J_0(A) + 2\sum_{j=1} J_{2j}(a)\cos(2j\omega t) \quad (34)$$

As seen from Equations (33)-(34), the Y basis function has no dc term if $J_0(A)=0$, which happens if the modulation amplitude A=2.4048 radians. In one embodiment, the modulation amplitude A is set to this value to simplify the analysis. In operation, the polarizer is set to ±45° with respect to the PEM and the analyzer is set to ±45° with respect to the plane of incidence. Assuming both are +45°, the intensity incident upon the detector 280 can be given as:

$$I(t)=I_0(R/4)\{1-SX-[\cos(2\theta_c)C+\sin(2\theta_c)N]Y\} \quad (35)$$

From this expression, it can be seen that two sample parameters can be measured at any one time. The $\sin(\omega t)$ Fourier coefficient is always proportional to the S parameter, and the $\cos(2\omega t)$ is proportional to either N or C, depending on the azimuthal angle of the PEM 260 ($\theta_c$).

It is possible to make a single PEM ellipsometer complete—that is, to measure N, S and C. One way to do this is via a two-channel spectroscopic polarization modulation ellipsometer (2-C SPME), where the single analyzer polarizer is replaced with a Wollaston prism. The Wollaston prism deviates the incident light beam into two mutually orthogonal linearly polarized light beams, both of which are detected with the 2-C SPME. If the azimuthal angle of the PEM is set to $\theta_c=\pm 22.5°$ and if the Wollaston prism is set at $\theta_a=\pm 45°$, then it is possible to measure N, S and C.

Figure 7:
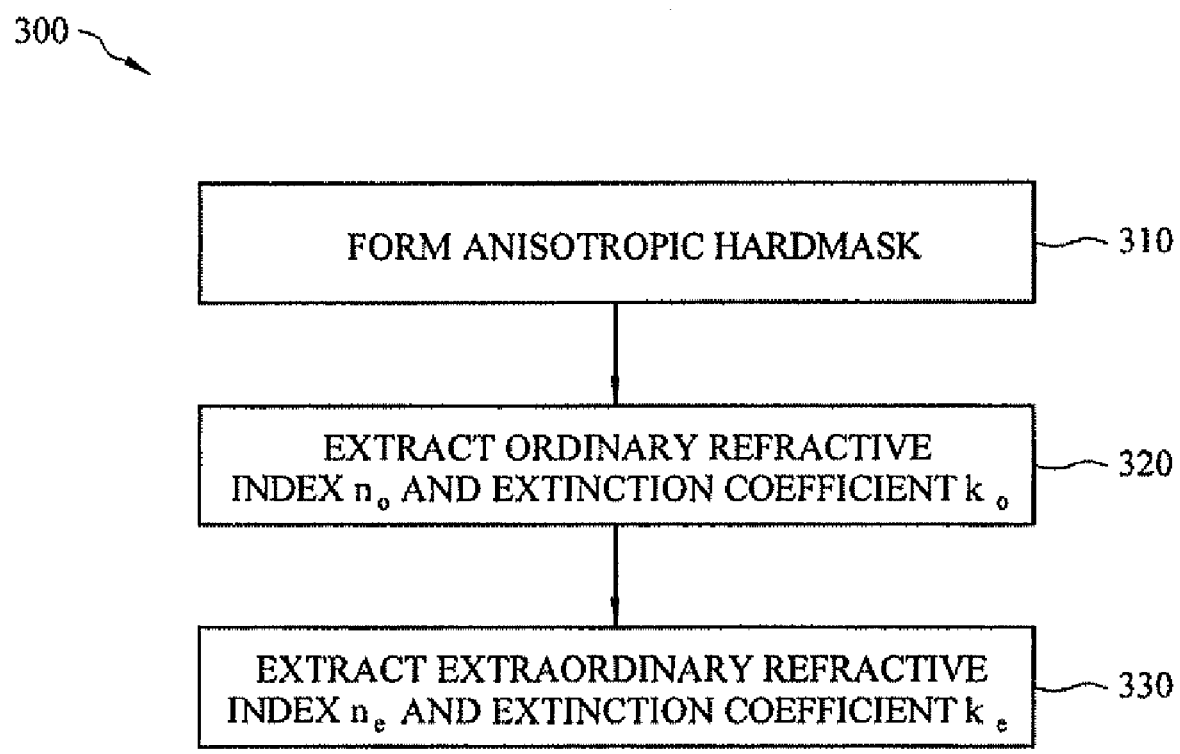
FIG. 7 is a flow-chart diagram of at least a portion of one embodiment of a method according to aspects of the present disclosure.

Referring to FIG. 7, illustrated is a flow-chart diagram of at least a portion of one embodiment of a method 300 according to aspects of the present disclosure. The method 300 may be employed or performed with measurement apparatus having one or more aspects similar to those described above with respect to FIGS. 3-6. In one embodiment, the method 300 is for extracting ordinary (p) and extraordinary (s) optical characteristics from an anisotropic sample (or portion thereof). For example, the sample may be or include a hardmask substantially comprising amorphous carbon and/or other anisotropic materials, and the method 300 may be employed to extract ordinary and extraordinary indices of refraction and/or extinction coefficients, which may then be employed to determine thickness, width, and/or other characteristics of the hardmask, possibly including characteristics other than dimensions. The extracted ordinary and extraordinary characteristics may also or alternatively be employed in optical and/or other CD measurement modeling and/or systems.

The method 300 includes a step 310 in which an anisotropic hardmask is formed by conventional or other means. For example, the hardmask may be formed by spin-on coating of an anisotropic photoresist material, such as amorphous carbon. The layer of photoresist may then be patterned and developed for subsequent use during etching of underlying layers. The photoresist may undergo one or more thermal treatments, such as to bake out any solvent and/or adjust selectivity.

In one embodiment, the hardmask is formed by or in conjunction with a dual deposition station processing chamber. However, the following description is merely exemplary of the aspects within the scope of the present disclosure, and should be interpreted accordingly. For example, flow rates may be total flow rates and, accordingly, may be divided in two to describe the process flow rates at each deposition station in a dual-station chamber. Additionally, or alternatively, single deposition chambers (such as the DxZ processing chamber that is commercially available from APPLIED MATERIALS, INC., of Santa Clara, Calif.) may be employed during the processing described below, with appropriate process conversions.

An amorphous carbon material may be deposited on a conductive material or conductive portion of a substrate by one or more processes, such as by introducing a gas mixture of one or more hydrocarbon compounds into a processing chamber. The hydrocarbon compound may have a formula substantially conforming to $C_xH_y$, where x has ranges between 2 and 4 and y ranges between 2 and 10. For example, propylene ($C_3H_6$), propane ($C_3H_8$), butane ($C_4H_{10}$), butylene ($C_4H_8$), butadiene ($C_4H_6$), or acetylene ($C_2H_2$), and/or combinations thereof, may be employed as the hydrocarbon compound.

Alternatively, partially or completely fluorinated derivatives of hydrocarbon compounds may be employed. For example, the fluorinated hydrocarbon compounds have a formula substantially conforming to $C_xH_yF_z$, where x ranges between 2 and 4, y ranges between 0 and 10, and z ranges between 0 and 10, with y+z greater than or equal to 2 and less than or equal to 10. Examples include fully fluorinated hydrocarbons, such as $C_3F_8$ or $C_4F_8$, which may be employed to deposit a fluorinated amorphous carbon layer or amorphous fluorocarbon layer. A combination of hydrocarbon compounds and fluorinated derivatives of hydrocarbon compounds may also or alternatively be employed to deposit the amorphous layer. Alternatively, hydrocarbon compounds and fluorinated derivatives thereof, including alkanes, alkenes, alkynes, cyclic compounds, and aromatic compounds, having five or more carbons, such as pentane, benzene, and toluene, may be employed to deposit the one or more amorphous layers.

Inert and reactive gases may be added to the gas mixture to modify properties of the amorphous material. The gases may be reactive gases, such as hydrogen ($H_2$), ammonia ($NH_3$), a mixture of hydrogen ($H_2$) and nitrogen ($N_2$), and/or combinations thereof. The addition of $H_2$ and/or $NH_3$ can be employed to control the hydrogen ratio of the amorphous layer to control layer properties, such as reflectivity. Inert gases, such as nitrogen ($N_2$), and noble gases, including Argon (Ar) and Helium (He), may be employed to control the density and deposition rate of the amorphous layer. A mixture of reactive gases and inert gases may also be added to the processing gas to deposit the amorphous layer.

The amorphous layer may be deposited from the processing gas by maintaining a substrate temperature ranging between about 100° C. and about 400° C., such as between about 250° C. and about 400° C., maintaining a chamber pressure ranging between about 1 Torr and about 20 Torr, introducing the hydrocarbon gas ($C_xH_y$) and any inert or reactive gases at a flow rate ranging between about 50 sccm and about 2000 sccm, and generating a plasma by applying a RF power ranging between about 0.03 W/cm$^2$ and about 20 W/cm$^2$, or between about 10 W and about 6000 W, for example between about 0.3 W/cm$^2$ and about 3 W/cm$^2$, or between about 100 W and about 1000 W, with a gas distributor being offset from the substrate surface by a distance ranging between about 200 mils and about 600 mils. The above process parameters provide one embodiment of a deposition rate for an amorphous carbon layer ranging between about 100 Å/min and about 5000 Å/min. The process can be implemented on a 200 mm substrate in a deposition chamber, although others are also within the scope of the present disclosure.

Alternatively, a dual-frequency system may be employed to deposit the amorphous material. A dual-frequency source of mixed RF power can provide a high frequency power ranging between about 10 MHz and about 30 MHz, as well as a low frequency power ranging between about 100 KHz and about 500 KHz. An example of a mixed frequency RF power application may include a first RF power with a frequency ranging between about 10 MHz and about 30 MHz at a power ranging between about 200 watts and about 800 watts and at least a second RF power with a frequency ranging between about 100 KHz and about 500 KHz at a power ranging between about 1 watt and about 200 watts. The ratio of the second RF power to the total mixed frequency power may range between about 0.6 and about 1.0, although in other embodiments the ratio may be less than about 0.6.

The amorphous layer may comprise carbon and hydrogen atoms, which may be an adjustable carbon:hydrogen ratio that ranges between about 10% hydrogen and about 60% hydrogen. The hydrogen ratio of the amorphous layer may be controlled to tune the respective optical properties, etch selectivity, and chemical mechanical polishing (CMP) resistance properties. As the hydrogen content decreases, the optical properties of the as-deposited layer may increase, such as for the index of refraction n and the extinction coefficient k. As the hydrogen content decreases, the etch resistance of the amorphous layer may increase.

The extinction coefficient k of the amorphous layer can be varied between about 0.1 and about 1.0 at wavelengths below about 250 nm, such as between about 193 nm and about 250 nm, which can make the amorphous carbon layer suitable for use as an anti-reflective coating (ARC) at DUV wavelengths, as well as visible wavelengths. The extinction coefficient k of the amorphous layer can additionally or alternatively be varied as a function of the deposition temperature. For example, as the temperature increases, the extinction coefficient k of the as-deposited layer may also increase, such as when propylene is the hydrocarbon compound and the extinction coefficient k for the as-deposited amorphous layer can be increased from about 0.2 to about 0.7 by increasing the deposition temperature from about 150° C. to about 480° C.

The extinction coefficient k of the amorphous layer can also be varied as a function of the additive used in the gas mixture. For example, the presence of hydrogen ($H_2$), ammonia ($NH_3$), and nitrogen ($N_2$), or combinations thereof, in the gas mixture can increase the extinction coefficient k by an amount ranging between about 10% and about 100%.

In an alternate embodiment, the amorphous layer can have an extinction coefficient k that varies across the thickness of the layer. That is, the amorphous layer can have an extinction coefficient k gradient formed therein. Such a gradient may be formed as a function of the variations of temperature and the composition of the gas mixture during layer formation.

At any interface between two material layers, reflections can occur because of differences in their refractive indices n and extinction coefficients k. When the amorphous ARC has a gradient, it is possible to match the refractive indices n and the extinction coefficients k of the two material layers so there is minimal reflection and maximum transmission into the amorphous ARC. Thereafter, the refractive index n and extinction coefficient k of the amorphous ARC can be gradually adjusted to absorb all of the light transmitted therein.

The amorphous layer may be deposited as two or more layers having different optical properties. For example, an amorphous carbon bi-layer may include a first amorphous carbon layer according to the process parameters described above and designed primarily for light absorption. As such, the first amorphous carbon layer may have an index of refraction ranging between about 1.5 and about 1.9, and an extinction coefficient k ranging between about 0.5 and about 1.0, at wavelengths less than about 250 nm. A second amorphous carbon layer, such as an anti-reflective coating layer, may be formed on the first amorphous carbon layer according to the process parameters described above. As such, the second amorphous carbon layer may have an index of refraction ranging between about 1.5 and about 1.9, and an absorption coefficient between about 0.1 and about 0.5. The second amorphous carbon layer may be designed primarily for phase shift cancellation by creating reflections that cancel those generated at the interface with an overlying material layer, such as an energy sensitive resist material. The refractive index n and the extinction coefficient k of the first and second amorphous carbon layers may be tunable in that they may be varied as a function of the temperature as well as the composition of the gas mixture during layer formation.

Removal of the amorphous material (whether before or after extraction of ordinary and extraordinary optical characteristics) may be achieved by subjecting the amorphous layer to a plasma of a hydrogen-containing gas and/or an oxygen-containing gas. The plasma of the hydrogen-containing gas and/or the oxygen-containing gas may remove the amorphous material with minimal effect of the dielectric and/or other materials of underlying layers.

The plasma treatment may include providing a hydrogen-containing gas including hydrogen, ammonia, water vapor ($H_2O$), or combinations thereof, to a processing chamber at a flow rate ranging between about 100 sccm and about 1000 sccm, such as between about 500 sccm and about 1000 sccm, and generating a plasma in the processing chamber. The plasma may be generated using a power density ranging between about 0.15 W/cm$^2$ and about 5 W/cm$^2$, or an RF power level ranging between about 50 W and about 1500 W. The RF power can be provided at a high frequency, such as between about 13 MHz and about 14 MHz. The RF power can be provided continuously or in short duration cycles wherein the power is on at the stated levels for cycles less than about 200 Hz and the on cycles total between about 10% and about 30% of the total duty cycle.

The plasma treatment may be performed by maintaining a chamber pressure ranging between about 1 Torr and about 10 Torr, such as between about 3 Torr and about 8 Torr, maintaining the substrate at a temperature ranging between about 100° C. and about 300° C. during the plasma treatment, such as between about 200° C. and about 300° C., for between about 15 seconds and about 120 seconds, or as necessary to remove the amorphous material with the gas distributor positioned at a distance ranging between about 100 mils and about 2000 mils from the substrate surface, such as a distance ranging between about 200 mils and about 1000 mils, during the plasma treatment. However, it should be noted that the parameters described above may be modified to perform the plasma processes in various chambers and for different substrate sizes, such as between 200 mm and 300 mm substrates. Alternatively, the plasma treatment process parameters may be the same or substantially the same as the material deposition process parameters.

In one embodiment, the anisotropic hardmask may be formed by or in conjunction with the APPLIED PRODUCER ADVANCED PATTERNING FILM (APF) PECVD SYSTEM that is commercially available from APPLIED MATERIALS, INC. The APPLIED PRODUCER APF system can be used, for example, to form a strippable hardmask on a substrate. The APPLIED PRODUCER APF system can form a dual layer stack consisting of a thin amorphous carbon layer with a thin DARC cap layer. The resulting CVD amorphous carbon hardmask can be highly selective for polysilicon and oxide etching with poly-to-carbon selectivity as high as 6:1, and oxide-to-carbon selectivity of 15:1. The APF may be easily stripped in an oxygen plasma ash, and both the carbon and DARC bi-layer may work as an anti-reflective coating for both 248 nm and 193 nm photolithography. The APF hardmask can be performed with as little as 100 nm of photoresist. In addition, the APF deposition process can eliminate the need for the wet chemical processing and treatment that are conventionally used in multi-layer resist process.

The method 300 also includes a step 320 in which the ordinary refractive index $n_o$ and the ordinary extinction coefficient $k_o$ are extracted, as well as a step 330 in which the extraordinary refractive index $n_e$ and the extraordinary extinction coefficient $k_e$ are extracted. However, as described above, the ordinary and extraordinary characteristics may be extracted substantially simultaneously. The ordinary refractive index $n_o$ may be regarded as the speed of propagation in the plane of incidence, the plane of greatest speed of propagation, and/or another plane/direction. In any case, the extraordinary refractive index $n_e$ may be regarded as the speed of propagation in a substantially different plane or direction, such as in a plane or direction that is substantially orthogonal to that of the ordinary refractive index $n_o$. For example, in one embodiment, the ordinary refractive index $n_o$ corresponds to the p-direction and the extraordinary refractive index $n_e$ corresponds to the s-direction, as described above with reference to FIG. 2. The ordinary and extraordinary extinction coefficients $k_o$ and $k_e$ may be similarly related.

In the embodiment depicted in FIG. 7, the ordinary and extraordinary characteristics $n_o$, $n_e$, $k_o$ and $k_e$ are extracted after the hardmask is substantially completed, but prior to use of the hardmask to etch underlying layers. However, in other embodiments, the optical characteristics of the hardmask may be extracted prior to the completion of the hardmask, as well as after one or more etching processes have been initiated and/or completed.

Figure 8:
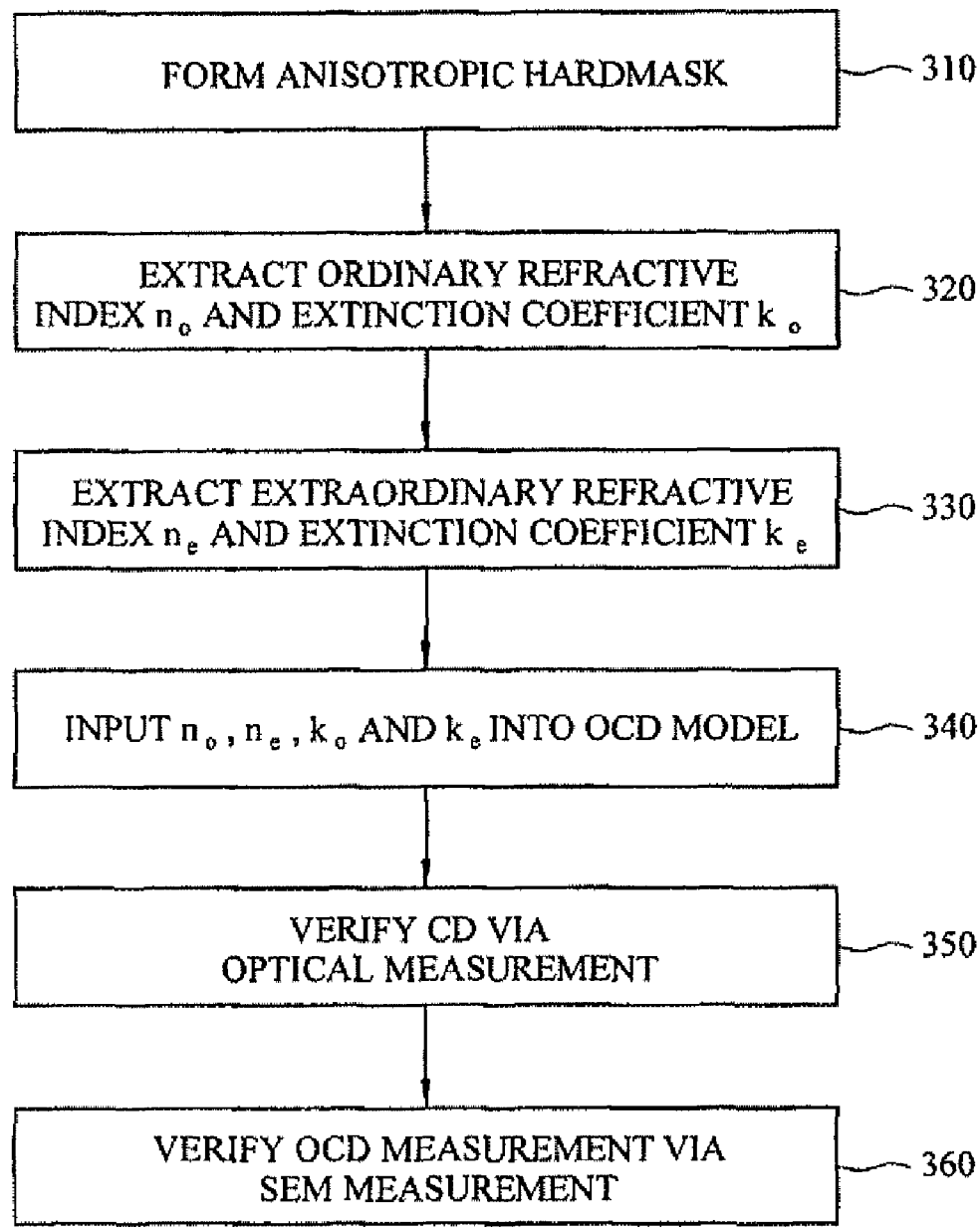
FIG. 8 is a flow-chart diagram of at least a portion of another embodiment of the method shown in FIG. 7.

Referring to FIG. 8, illustrated is a flow-chart diagram of another embodiment of the method 300 shown in FIG. 7, herein designated by the reference numeral 305. The method 305 is substantially similar to the method 300 shown in FIG. 7, in that the method 305 includes the steps 310, 320 and 330 described above. However, the method 305 also includes a step 340 in which the ordinary and extraordinary characteristics $n_o$, $n_e$, $k_o$ and $k_e$ are input into an optical critical dimension (OCD) model. The OCD model may describe the geometric dimensions and/or optical characteristics of the hardmask, one or more layers underlying the hardmask, and/or one or more features defined during etch processing employing the hardmask. In one embodiment, the OCD model accounts for all layers in the sample structure being characterized, measured, or verified by the optical CD measuring system. The OCD model may be subsequently employed in a step 350 during which critical dimensions (CDs) of the hardmask and/or underlying features are optically verified. The optically-verified CDs may then be verified via a scanning electron microscope (SEM) in a step 360.

Figure 9:
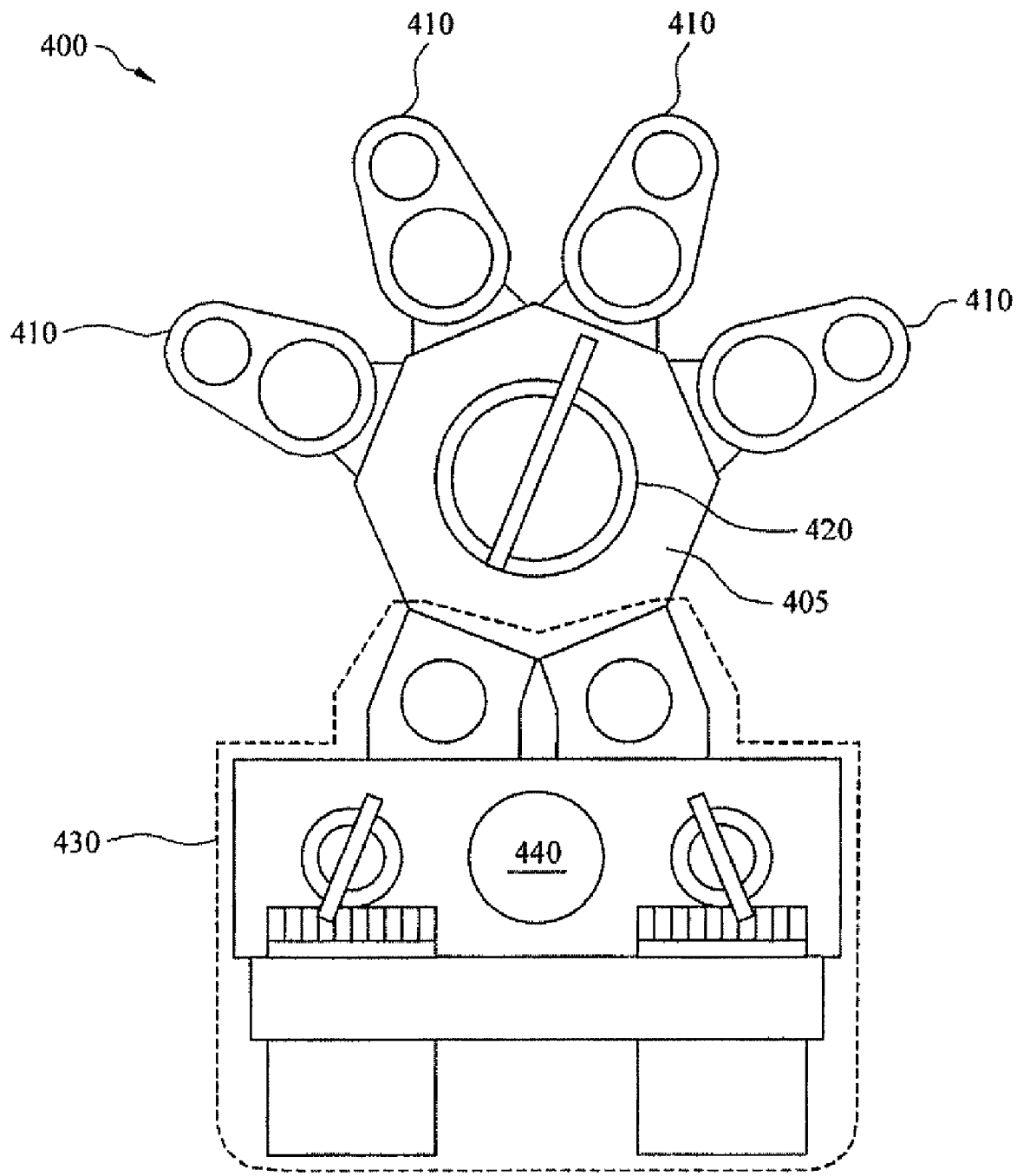
FIG. 9 is a schematic view of at least a portion of one embodiment of apparatus according to aspects of the present disclosure.

Referring to FIG. 9, illustrated is a schematic view of at least a portion of one embodiment of apparatus 400 according to one or more aspects of the present disclosure. The apparatus 400, which may generally resemble a cluster tool, may be employed with or during the method 300 shown in FIG. 7 and/or the method 305 shown in FIG. 8. That is, the apparatus 400 may be employed to verify CDs of a hardmask or other features formed on a substrate, including those formed within the apparatus 400.

The apparatus 400 includes four process chambers 410, although other embodiments may include more or less than four process chambers 410. Each process chamber 410 is configured to perform one or more semiconductor fabrication processes, such as deposition and/or etching processes. For example, each chamber 410 may be configured to perform chemical vapor deposition (CVD), plasma enhanced CVD (PECVD), and/or physical vapor deposition (PVD), among others. One or more of the chambers 410 may additionally or alternatively be configured to perform rapid thermal annealing and/or other heat treatment processes.

The apparatus 400 also includes wafer transfer means 420 housed within a central chamber or staging area 405. The wafer transfer means 420 are configured to transfer process wafers between the chambers 410 and load-lock means 430. The wafer transfer means 420 and/or the load-lock means 430 may be partially or fully automated.

The apparatus 400 also includes CD measurement means 440. The CD measurement means 440 may be integral to the apparatus 400 such that CDs of features on wafers processed within the apparatus 400 may be examined without requiring the removal of the wafer from the apparatus 400. That is, the CD measurement means 440 may be configured to perform in-situ CD measurement. Methods by which CDs may be measured via CD measurement means 440 may be substantially similar to those described above, including via the extraction of both ordinary and extraordinary optical characteristics. The CD measurement means 440 may include optical and/or SEM CD measurement means, among others, including those described above (e.g., with respect to FIGS. 3-6).

In the embodiment depicted in FIG. 9, the CD measurement means 440 are integral to the load-lock area of the apparatus 400. Consequently, CD measurements may be performed prior to and/or after one or more processes are performed within the apparatus 400, including at intermediate points between processes.

Figure 10:
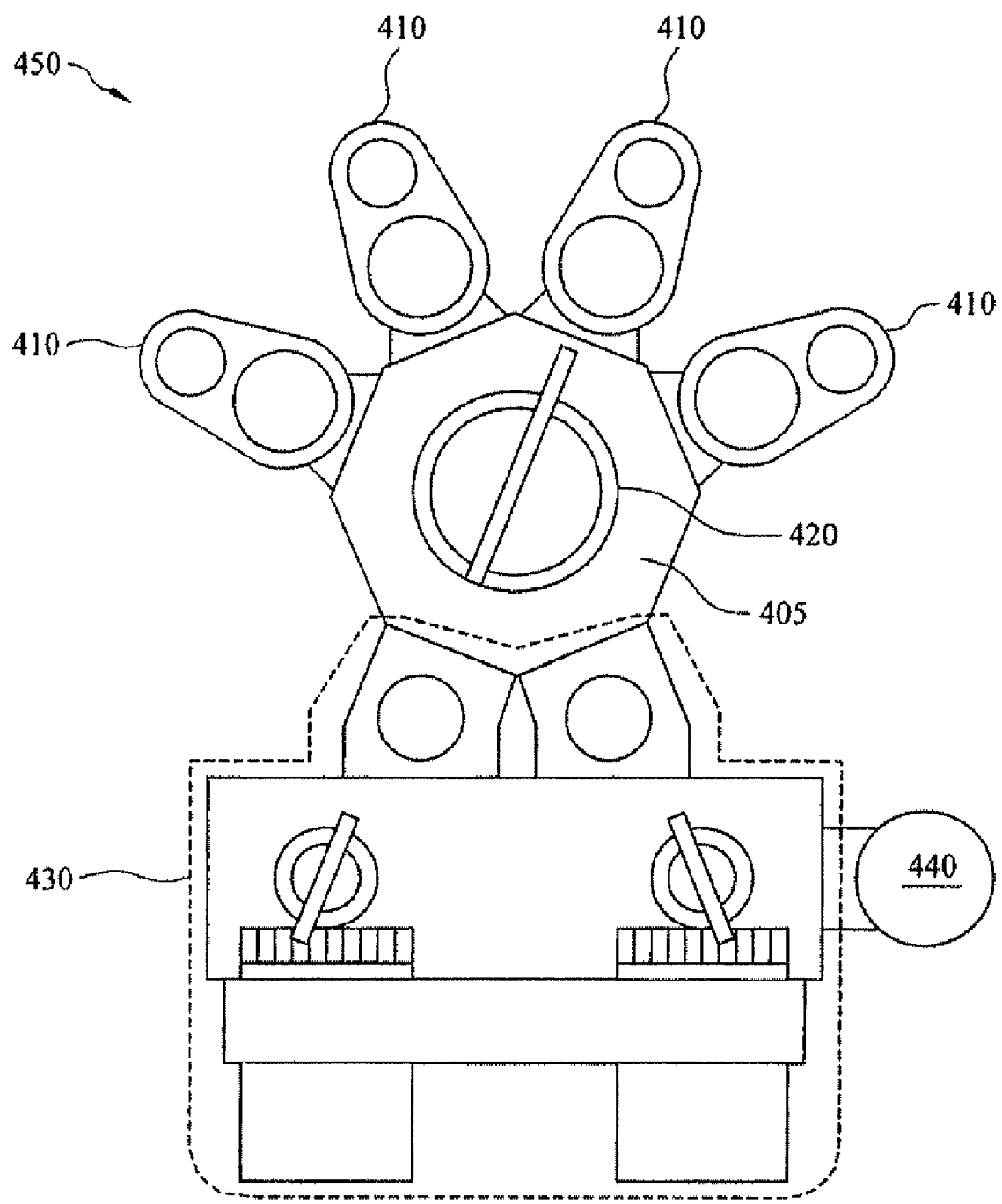
FIG. 10 is a schematic view of at least a portion of another embodiment of the apparatus shown in FIG. 9.

Referring to FIG. 10, illustrated is a schematic view of at least a portion of another embodiment of the apparatus 400 shown in FIG. 9, herein designated by the reference numeral 450. The apparatus 450 is substantially similar to the apparatus 400 shown in FIG. 9, such as in the similar inclusion of a number of process chambers 410, wafer transfer means 420, load-lock means 430 and CD measurement means 440. However, the CD measurement means 440 of apparatus 450 is externally coupled to the load-lock means 430, in contrast to the integral arrangement of apparatus 400. Nonetheless, CD measurement may still be performed in-situ, as the load-lock means 430 may be configured to transfer wafers to and from the CD measurement means 440.

Figure 11:
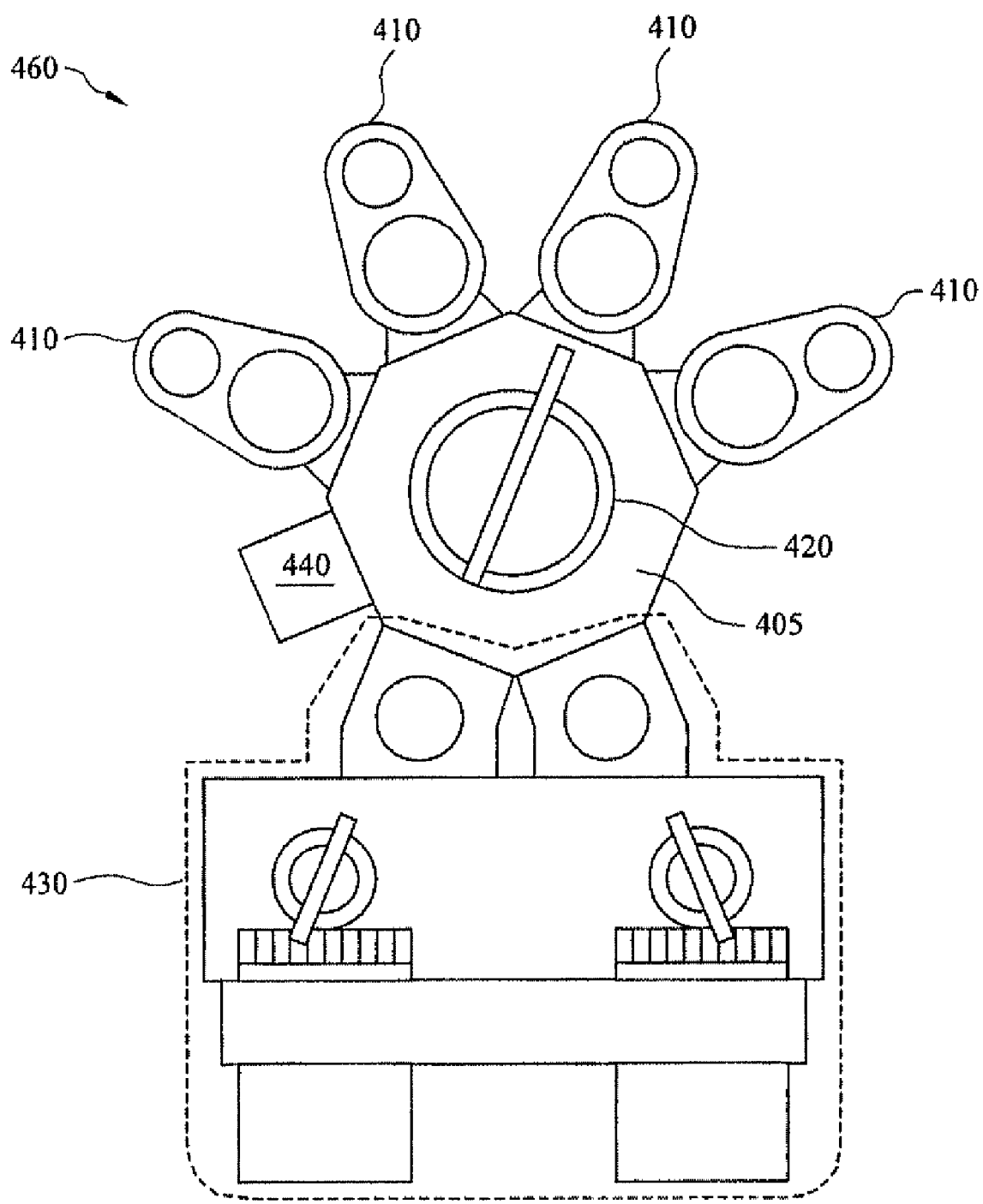
FIG. 11 is a schematic view of at least a portion of yet another embodiment of the apparatus shown in FIG. 9.

Referring to FIG. 11, illustrated is a schematic view of at least a portion of another embodiment of the apparatus 400 shown in FIG. 9, herein designated by the reference numeral 460. The apparatus 460 is substantially similar to the apparatus 400 shown in FIG. 9, such as in the similar inclusion of a number of process chambers 410, wafer transfer means 420, load-lock means 430 and CD measurement means 440. However, the CD measurement means 440 of apparatus 460 is externally coupled to the center chamber 405, in contrast to the arrangement of apparatus 400. Nonetheless, CD measurement may still be performed in-situ, as the wafer transfer means 420 may be configured to transfer wafers to and from the CD measurement means 440.

Figure 12:
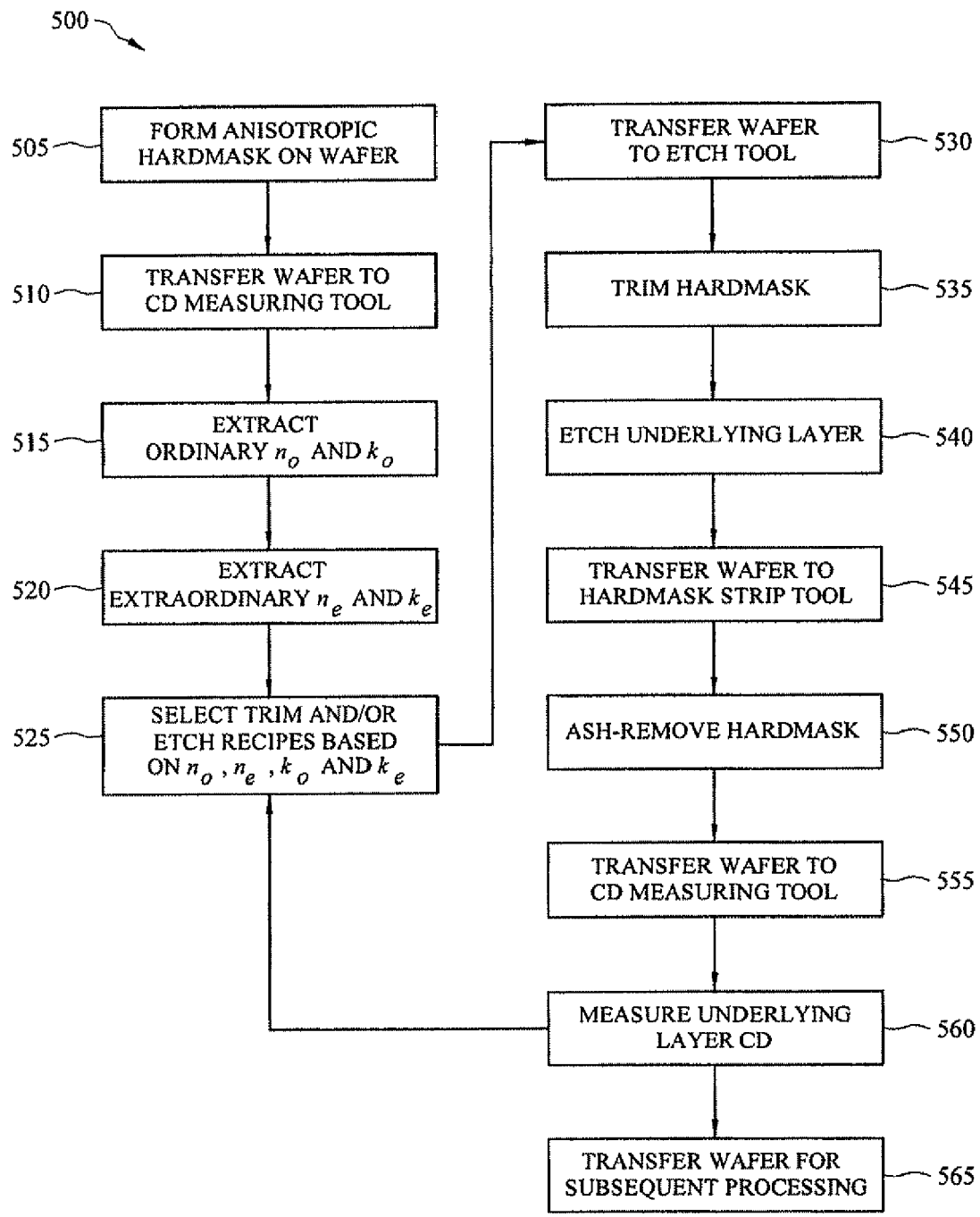
FIG. 12 is a flow-chart diagram of at least a portion of one embodiment of a method according to aspects of the present disclosure.

Referring to FIG. 12, illustrated is a flow-chart diagram of at least a portion of one embodiment of a method 500 according to aspects of the present disclosure. The method 500 is one example of operations that may be performed via the apparatus 400, 450 and/or 460 shown in FIGS. 9-11, among others within the scope of the present disclosure. One or more aspects of the method 500 may be substantially similar to those of the methods 300 and 305 shown in FIGS. 7 and 8, among others within the scope of the present disclosure.

The method 500 includes a step 505 in which an amorphous carbon or other anisotropic hardmask is formed on a wafer. Aspects of the step 505 may be substantially similar to those of step 310 shown in FIGS. 7 and 8, and may include processing/operations within one or more chambers of a cluster tool, such as the chambers 410 of the apparatus 400, 450 and 460 shown in FIGS. 9-11.

In a subsequent step 510, the wafer is transferred to a CD measurement tool. For example, wafer transfer means (e.g., wafer transfer means 420 shown in FIGS. 9-11) and/or load-lock means (e.g., load-lock means 430 shown in FIGS. 9-11) may independently or cooperatively transfer the wafer to a CD measurement tool (e.g., CD measurement means 440 shown in FIGS. 9-11) which may be integral to or coupled to the apparatus in which the wafer is being processed. Thereafter, the CD measurement tool may be employed to extract the ordinary index of refraction $n_o$ and extinction coefficient $k_o$ of a hardmask and/or one or more other features and/or layers on the wafer during a step 515, possibly including several such measurements (e.g., time- and/or wavelength-dependent measurements). Step 515 may be substantially similar to step 320 shown in FIGS. 7 and 8.

While the wafer is in the CD measurement tool, the extraordinary index of refraction $n_e$ and extinction coefficient $k_e$ of the hardmask, feature(s) and/or layer(s) on the wafer may also be extracted during a step 520, possibly including several such measurements (e.g., time- and/or wavelength-dependent measurements). Step 520 may be substantially similar to step 330 shown in FIGS. 7 and 8. Moreover, at least in one embodiment, steps 515 and 520 may be performed substantially simultaneously.

In a subsequent step 525, one or more process recipes for trimming, etching and/or otherwise processing the hardmask, feature(s) and/or layer(s) on the wafer are selected, calculated or otherwise determined, based on the optical characteristics extracted during steps 515 and 520. The wafer is then transferred to an etching or other processing tool in step 530, where such tool may be substantially similar to one of the chambers 410 shown in FIGS. 9-11, and where such transfer may be performed by means such as wafer transfer means 420 and/or load-lock means 430 also shown in FIGS. 9-11. The hardmask, feature(s) and/or layer(s) on the wafer may then be trimmed in a step 535, etched in a step 540, or otherwise processed, possibly based on the optical characteristics extracted during steps 515 and 520.

The wafer may subsequently be transferred to a stripping tool in a step 545, such as via wafer transfer means 420 and/or load-lock means 430 shown in FIGS. 9-11. The stripping tool may be a chamber of a cluster tool, such as one of the chambers 410 shown in FIGS. 9-11. Thereafter, a step 550 may be performed to remove at least a portion of one or more of the hardmask, feature(s) and/or layer(s) on the wafer. For example, step 550 may include plasma ashing, in which oxygen and a fluorocarbon (e.g., $CF_4$ or $C_2F_6$) are employed to strip the hardmask from the wafer. The stripping tool may be or include a plasma etch tool, such as a barrel type tool where a plasma is generated in the same chamber as the substrate, or a downstream type tool in which a plasma is generated in one chamber and is directed towards the wafer in a second chamber through a tube or an inlet. The plasma source may be an inductively coupled plasma (ICP) source or a transformer coupled plasma (TCP) source, among others.

An oxygen plasma may be employed to strip the hardmask and/or other feature(s) on the wafer since the oxygen radicals react with C, H, S, and N in polymer and photosensitive material components to afford their respective oxides, which are volatile. However, pure $O_2$ plasma may not always sufficiently strip the hardmask and/or other feature(s) on the wafer, such that $C_2F_6$ may be combined with $O_2$ in a first plasma etch step and then followed with an $O_2$-only ashing step to more thoroughly remove the hardmask and/or other feature(s) on the wafer. In one embodiment, water is employed as an oxygen and hydrogen source and combined with $CF_4$ in a first plasma ash step and $O_2$ plasma is then used in a second step to complete the stripping process.

The stripping performed during step 550 may also or alternatively include a low-temperature stripping method, such as may involve an oxidizing gas, a halide containing gas and a hydrocarbon. One such embodiment may utilize $SO_3$ by itself or combined with oxygen and/or other etching gases. For example, a low-temperature hardmask strip process involving $O_2$ and a fluorocarbon plasma etch may be employed.

In one embodiment, the stripping performed in step 550 may employ a plasma treatment which includes oxygen and one or more fluorocarbon gases $C_xH_yF_z$ where x, y and z are integers, such as $CH_3F$, $CH_2F_2$, and $CHF_3$. Furthermore, the gas mixture used to generate the plasma may be additionally comprised of $N_2$ or $N_2H_4$. Optionally, the plasma treatment is performed without oxygen.

As an example of the stripping performed during step 550, the wafer may be fastened to a chuck in a process chamber that is part of the stripping tool, and a vacuum is applied to remove all gases from the process chamber. Plasma may be generated in the chamber from an RF discharge source and bias power, or from a microwave downstream plasma flow, as in an asher. However, other chamber architectures and plasma delivery systems are also within the scope of the present disclosure. The plasma may be generated in the process chamber by first purging the chamber and subsequently introducing oxygen, possibly at a flow rate ranging between about 200 and about 10,000 sccm, and one or more $C_xH_yF_z$ gases, such as $CH_3F$, $CH_2F_2$, and $CHF_3$ each with a flow rate ranging between about 1 and about 500 sccm, all flowed into the process chamber while the wafer is heated to a temperature ranging between about 20° C. and about 300° C. The ratio of oxygen flow rate to $C_xH_yF_z$ flow rate may range between about 10:1 and about 1000:1. The combined gas flow may provide a pressure range between about 10 mtorr and about 5 torr in the process chamber. Once the desired temperature is reached, a plasma can be struck by applying an RF power ranging between about 200 W and about 2000 W. The plasma treatment is continued while the temperature is maintained between about 20° C. and about 300° C. for a predetermined amount of time or until end point detection. The wafer may subsequently be cleaned with a DI-rinse and/or other cleaning methods.

In a step 555, the wafer may be transferred to a CD measurement tool, as described above with respect to step 510. One or more CDs of the underlying layer that was patterned with the hardmask may be measured in a subsequent step 560. If additional processing is required, such as may be indicated by the results of the measurements taken during step 560, one or more of steps 525-555 may be repeated. However, the method may alternatively proceed to a step 565, during which the wafer may be transferred for additional processing, whether within the same apparatus or other apparatus.

Figure 13:
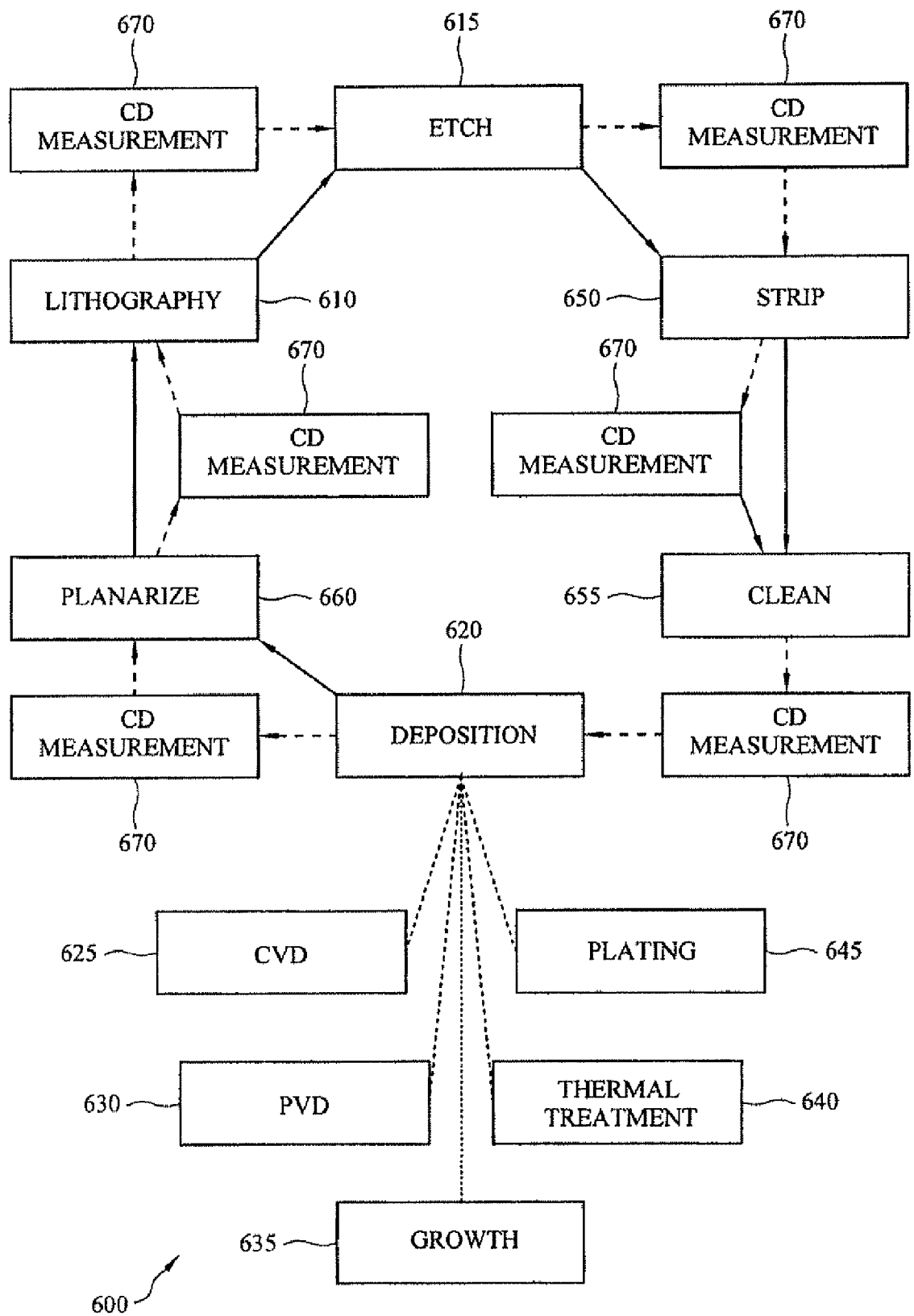
FIG. 13 is a flow-chart diagram of at least a portion of another embodiment of the method shown in FIG. 12.

Referring to FIG. 13, illustrated is a flow-chart diagram of another embodiment of the method 500 shown in FIG. 12, herein designated by the reference numeral 600. The method 600 includes one or more lithography steps 610 during which one or more layers of photoresist material are patterned, one or more etching steps 615 during which the pattern of one or more layers is transferred to one or more underlying metal and/or dielectric layers, and one or more deposition steps 620 during which one or more photoresist, metal and/or dielectric layers are formed over a wafer or substrate. The one or more deposition steps 620 may include performing one or more CVD processes 625, one or more PVD processes 630, one or more growth processes 635 (e.g., in-situ growth, selective epitaxial growth, and others), one or more thermal treatment processes 640 (e.g., rapid-thermal-annealing, and others), and/or one or more plating processes 645 (e.g., electroplating, silicide formation, and others).

The method 600 may also include one or more stripping steps 650 during which at least portions of one or more previously-formed layers are removed, as well as one or more cleaning steps 655 during which residue, particulate and/or contaminants may be removed by one or more wet or dry processes. The method 600 may also include one or more planarizing steps 660 during which one or more previously-formed layers may be chemically and/or mechanically planarized (e.g., CMP) to provide substantially planar surfaces, such as in preparation for subsequent processing.

The method 600 also includes at least one CD measurement step 670 interposing ones of the above-described steps 610, 615, 620, 650, 655 and 660, as indicated by the dashed arrows schematically interconnecting these steps. The CD measurement step 670 include measurement by apparatus having one or more aspects that are substantially similar to those of apparatus shown in FIGS. 3-6 and/or 9-11. The CD measurement step 670 may also or alternatively include measurement by one or more methods having one or more aspects that are substantially similar to those of steps 320 and 330 shown in FIG. 7, steps 320-360 shown in FIG. 8, and/or steps 515, 520 and 560 shown in FIG. 12.

For example, as in the embodiment depicted in FIG. 13, the method 600 may include a CD measurement step 670 interposing the one or more lithography steps 610 and the one or more etch steps 615, such that the method 600 may proceed from lithography to CD measurement and then to etching, in contrast to proceeding from lithography directly to etching. Similarly, the method 600 may also or alternatively include a CD measurement step 670 interposing the one or more etch steps 615 and the one or more stripping steps 650 (when performed), such that the method 600 may proceed from etching to CD measurement and then to stripping, in contrast to proceeding from etching directly to stripping. The method 600 may also or alternatively include a CD measurement step 670 interposing the one or more stripping steps 650 (when performed) and the one or more cleaning steps 655 (when performed), such that the method 600 may proceed from stripping to CD measurement and then to cleaning, in contrast to proceeding from stripping directly to cleaning.

The method 600 may also or alternatively include a CD measurement step 670 interposing the one or more cleaning steps 655 (when performed) and the one or more deposition steps 620, such that the method 600 may proceed from cleaning to CD measurement and then to deposition, in contrast to proceeding from cleaning directly to deposition. The method 600 may also or alternatively include a CD measurement step 670 interposing the one or more deposition steps 620 and the one or more planarizing steps 660 (when performed), such that the method 600 may proceed from deposition to CD measurement and then to planarization, in contrast to proceeding from deposition directly to planarization. The method 600 may also or alternatively include a CD measurement step 670 interposing the one or more planarizing steps 660 (when performed) and the one or more lithography steps 610, such that the method 600 may proceed from planarizing to CD measurement and then to lithography, in contrast to proceeding from planarizing directly to lithography.

The cycle of lithography 610, etch 615, strip 650 (when performed), clean 655 (when performed), deposition 620 and planarization 660 (when performed) may be repeated a number of times during the manufacture of an integrated circuit device. Each such cycle may result in the formation of a hardmask or other photoresist layer, a metal layer, a dielectric layer, and/or a semiconductor layer, or multiples thereof, including where such layers may ultimately define a number of discrete members or otherwise be patterned. However, each cycle may not include the same sequence of steps 610-615-650-655-620-660, as some cycles may exclude one or more of such steps, may include a different sequence, and/or may include additional steps not illustrated in FIG. 13. In addition, each cycle may not include a CD measurement step 670 between each of the steps 610-615-650-655-620-660 in a particular sequence. For example, one or more cycles may include only one or two CD measurement steps 670, whereas other cycles may include a greater number of CD measurement steps 670, and one or more other cycles may not include any CD measurement steps 670.

It is evident from the description above and the following claims that the present disclosure introduces a method of measuring a critical dimension of an optically-anisotropic feature, the method comprising extracting a number of values each descriptive of the optically-anisotropic feature, including values corresponding to ordinary and extraordinary measurements of one or more optical characteristics of the optically-anisotropic feature. The optical characteristics can include the index of refraction and/or the extinction coefficient of the optically-anisotropic feature, among others. Additionally, the values can be input into an optical critical dimension (OCD) measurement model, such that the critical dimension can be verified via optical measurement based on the OCD measurement model. The optical measurement of the critical dimension can also be verified via scanning electron microscope (SEM) measurement. Furthermore, the optically-anisotropic feature may have a substantially amorphous composition, such as amorphous carbon, including where the optically-anisotropic feature is that of a hardmask substantially comprising amorphous carbon or otherwise having a substantially amorphous composition.

Another embodiment of a method of measuring a critical dimension of an optically-anisotropic feature according to aspects of the present disclosure includes extracting a first optical characteristic of the optically-anisotropic feature, wherein the first optical characteristic is one of an ordinary index of refraction and an ordinary extinction coefficient of the optically-anisotropic feature. The method also includes extracting a second optical characteristic of the optically-anisotropic feature, wherein the second optical characteristic is one of an extraordinary index of refraction and an extraordinary extinction coefficient of the optically-anisotropic feature.

For example, the first optical characteristic may be the ordinary index of refraction of the optically-anisotropic feature and the second optical characteristic may be the extraordinary index of refraction of the optically-anisotropic feature. In another example, the first optical characteristic may be the ordinary extinction coefficient of the optically-anisotropic feature and the second optical characteristic may be the extraordinary extinction coefficient of the optically-anisotropic feature.

The method may also include extracting a third optical characteristic of the optically-anisotropic feature. In one embodiment, the third optical characteristic is one of the ordinary extinction coefficient and the extraordinary extinction coefficient of the optically-anisotropic feature, while in another embodiment the third optical characteristic is one of the ordinary index of refraction and the extraordinary index of refraction of the optically-anisotropic feature. The method may also include extracting a fourth optical characteristic of the optically-anisotropic feature, such that the first, second, third and fourth optical characteristics collectively include the ordinary and extraordinary indices of refraction and extinction coefficients of the optically-anisotropic feature.

The present disclosure also introduces a cluster tool operable in the fabrication of a microelectronic device. In one embodiment, the cluster tool includes a plurality of integrated process chambers each configured to process a wafer. The cluster tool also includes means for optically measuring a critical dimension of an optically-anisotropic feature formed on the wafer without removing the wafer from the cluster tool, including means for extracting ordinary and extraordinary optical characteristics of the optically-anisotropic feature. The cluster tool also includes means for transferring the wafer between ones of the process chambers and the critical dimension measuring means. In one embodiment, the plurality of process chambers includes at least one chamber operable to form a substantially amorphous hardmask comprising the optically-anisotropic feature, as well as at least one chamber operable for ash-removal of the hardmask. At least one chamber may be operable to form an amorphous carbon hardmask comprising the optically-anisotropic feature. The cluster tool may also include means for loading and unloading the wafer into a wafer staging area of the cluster tool, wherein the critical dimension measuring means is integral to the loading and unloading means.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A method of measuring a critical dimension of an optically-anisotropic feature, comprising:
    extracting a first value descriptive of the optically-anisotropic feature; and
    extracting a second value descriptive of the optically-anisotropic feature, wherein
    the first value corresponds to an ordinary measurement of an optical characteristic of the optically-anisotropic feature, and
    the second value corresponds to an extraordinary measurement of the optical characteristic of the optically-anisotropic feature;
    analyzing the first and second values using an optical critical dimension (OCD) measurement model; and
    verifying the critical dimension via optical measurement based on the analyzing using the OCD measurement model.

2. The method of claim 1 wherein the optical characteristic is one of:
    an index of refraction of the optically-anisotropic feature, and
    an extinction coefficient of the optically-anisotropic feature.

3. The method of claim 1 further comprising extracting third and fourth values descriptive of the optically-anisotropic feature, wherein:
    the first value corresponds to an ordinary measurement of an index of refraction of the optically-anisotropic feature, the second value corresponds to an extraordinary measurement of the index of refraction of the optically-anisotropic feature, the third value corresponds to an ordinary measurement of an extinction coefficient of the optically-anisotropic feature, and the fourth value corresponds to an extraordinary measurement of the extinction coefficient of the optically-anisotropic feature.

4. The method of claim 1 further comprising verifying the optical measurement of the critical dimension via scanning electron microscope (SEM) measurement.

5. The method of claim 1 wherein the optically-anisotropic feature has a substantially amorphous composition.

6. The method of claim 1 wherein the optically-anisotropic feature substantially comprises amorphous carbon.

7. The method of claim 1 wherein the optically-anisotropic feature is a hardmask having a substantially amorphous composition.

8. The method of claim 1 wherein the optically-anisotropic feature is a hardmask substantially comprising amorphous carbon.

9. A method of measuring a critical dimension of an optically-anisotropic feature, comprising:

extracting a first optical characteristic of the optically-anisotropic feature, wherein the first optical characteristic is one of
an ordinary index of refraction of the optically-anisotropic feature, and
an ordinary extinction coefficient of the optically-anisotropic feature; and extracting a second optical characteristic of the optically-anisotropic feature, wherein the second optical characteristic is one of:
an extraordinary index of refraction of the optically-anisotropic feature, and
an extraordinary extinction coefficient of the optically-anisotropic feature;

analyzing the first and second values using an optical critical dimension (OCD) measurement model; and verifying the critical dimension via optical measurement based on the analyzing using the OCD measurement model.

10. The method of claim 9 wherein:
the first optical characteristic is the ordinary index of refraction of the optically-anisotropic feature, and
the second optical characteristic is the extraordinary index of refraction of the optically-anisotropic feature.

11. The method of claim 10 further comprising extracting a third optical characteristic of the optically-anisotropic feature, wherein the third optical characteristic is one of:
the ordinary extinction coefficient of the optically-anisotropic feature, and
the extraordinary extinction coefficient of the optically-anisotropic feature.

12. The method of claim 11 further comprising extracting a fourth optical characteristic of the optically-anisotropic feature, wherein:
the third optical characteristic is the ordinary extinction coefficient of the optically-anisotropic feature, and
the fourth optical characteristic is the extraordinary extinction coefficient of the optically-anisotropic feature.

13. The method of claim 9 wherein:
the first optical characteristic is the ordinary extinction coefficient of the optically-anisotropic feature, and
the second optical characteristic is the extraordinary extinction coefficient of the optically-anisotropic feature.

14. The method of claim 13 further comprising extracting a third optical characteristic of the optically-anisotropic feature, wherein the third optical characteristic is one of:
the ordinary index of refraction of the optically-anisotropic feature, and
the extraordinary index of refraction of the optically-anisotropic feature.

15. A cluster tool operable in the fabrication of a microelectronic device, comprising:
a plurality of integrated process chambers each configured to process a wafer;
means for optically measuring a critical dimension of an optically-anisotropic feature formed on the wafer without removing the wafer from the cluster tool, including means for extracting ordinary and extraordinary optical characteristics of the optically-anisotropic feature, wherein the critical dimension measuring means is coupled to a central chamber comprising a transfer chamber; and
means for transferring the wafer between ones of the process chambers and the critical dimension measuring means.

16. The cluster tool of claim 15 wherein the plurality of process chambers includes:
at least one chamber operable to form a substantially amorphous hardmask comprising the optically-anisotropic feature, and
at least one chamber operable for ash-removal of the hardmask.

17. The cluster tool of claim 15 wherein the plurality of process chambers includes at least one chamber operable to form an amorphous carbon hardmask comprising the optically-anisotropic feature.

18. The cluster tool of claim 15 further comprising means for loading and unloading the wafer into a wafer staging area of the cluster tool, wherein the critical dimension measuring means is integral to the loading and unloading means.

* * * * *